United States Patent [19]
Harris

[11] Patent Number: 5,851,997
[45] Date of Patent: *Dec. 22, 1998

[54] USE OF HUMAN CHORIONIC GONADOTROPIN AS AN IMMUNE-POTENTIATING ANTIVIRAL AGENT

[76] Inventor: Pamela Jo Harris, 1810 Calvert St. NW. Suite #5, Washington, D.C. 20009

[ * ] Notice: The term of this patent shall not extend beyond the expiration date of Pat. No. 5,700,781.

[21] Appl. No.: 676,518

[22] Filed: Jul. 2, 1996

Related U.S. Application Data

[63] Continuation-in-part of Ser. No. 338,166, Nov. 10, 1994, Pat. No. 5,700,781, which is a continuation-in-part of Ser. No. 317,909, Oct. 4, 1994, abandoned.

[60] Provisional application No. 60/000,946 Jul. 7, 1995.

[51] Int. Cl.[6] .......................... A61K 38/00; A61K 39/21; C07K 1/00
[52] U.S. Cl. .................................... 514/21; 514/2; 514/8; 514/12; 514/885; 514/934; 424/188.1; 424/205.1; 530/324; 530/397; 530/398; 530/399; 530/828
[58] Field of Search .............................. 514/21, 2, 8, 12, 514/885, 934; 424/188.1, 208.1; 530/324, 397, 398, 399, 828

[56] References Cited

U.S. PATENT DOCUMENTS

| | | | |
|---|---|---|---|
| 4,692,332 | 9/1987 | McMichael | 424/88 |
| 4,877,610 | 10/1989 | McMichael | 424/88 |
| 4,880,626 | 11/1989 | McMichael | 424/88 |
| 4,966,753 | 10/1990 | McMichael | 424/88 |
| 4,970,071 | 11/1990 | McMichael | 424/88 |

OTHER PUBLICATIONS

Cohen *Is a New Virus the Cause of KS?* Science, 266:1803–4 (1994).
Chang *Identification of Herpesvirus–Like DNA Sequences in AIDS–Associated Kaposi's Sarcoma* Science, 266:1865–9 (1994).
Rosenthal *Maladie de Kaposi et hormones sexuelles: à propos d'une observation, revue de la littérature* Rev Méd Interne 15:186–9 (1994).
Ambroziak *Herpes–Like Sequences in HIV–Infected and Uninfected Kaposi's Sarcoma Patients* Science 268:582–3 (1995).
Lunardi–Iskandar *Tumorigenesis and metastasis of neoplastic Kaposi's sarcoma cell line in immunodeficient mice blocked by a human pregnancy hormone* Nature 375:64–8 (1995).
Ritter *Pregnancy Hormone May Treat AIDS–Related Condition, Report Suggests* (1995) Associated Press.
Monfardini *Treatment of acquired immunodeficiency syndrome (AIDS)–related cancer* Cancer Treatment Reviews 20:149–172 (1994).
Lilenbaum *Systemic Treatment of Kaposi's sarcoma: current status and future directions* AIDS 8:141–151 (1994).
10th International AIDS meeting, Yokohama, Japan (1994).
*HCG and Kaposi's Sarcoma* Pl Perspectives . . . Nov. 1994.
Stein *Aids Related Kaposi's Sarcoma: A Review*, Israel Journal of Medical Sciences, 30:298–305 (1994).
Harris *Human Chorionic Gonadotropin Hormone Is Antiviral* Medical Hypotheses 47:71–72 (1996).
Cohen *Controversy: Is KS Really Caused By New Herpesvirsu?* (1995) Science 268:1847–8.
Bourinbaiar et al, FEBS. LETS, vol. 309, No. 1, pp. 82–84, Aug. 1992.
Gold, *Treatment Science*, vol. 8, No. 7, pp. 1–2, 1994.
"New Directions Needed for AID Research," *Computer Dialog*, PHIND (Archival), Aug. 19, 1994.
Sandstrom et al., *Review Articles in Drugs*, vol. 34, pp. 373–390, 1987.
Haynes, *Science*, vol. 260, pp. 1279–1286, 28 May 1993.
Fox, *Bio/Technology*, vol. 12, p. 128, 12 Feb. 1994.
Brown, *The Washington Post*, Jun. 10, 1993.

*Primary Examiner*—Cecilia J. Tsang
*Assistant Examiner*—Abdel A. Mohamed
*Attorney, Agent, or Firm*—Foley & Lardner

[57] ABSTRACT

Prophylaxis against viral infections, as well as treatment for individuals infected with a virus, can be achieved through the administration of human chorionic gonadotropin (HCG). Exemplary of the viral infections that are amenable to the use of HCG in this regard include those caused by HIV-1, Kaposi's sarcoma herpes virus, molluscipoxvirus and cytomegalovirus. In addition, HCG can be used as a neonatal immune booster via administration to a baby at delivery and, optionally, for the first several months of life, until the infantile immune system matures, in order to prevent HIV transmission and control any low-level viremia, as well as to protect against various other viruses, such as herpes viruses and oncogenic viruses.

11 Claims, No Drawings

USE OF HUMAN CHORIONIC GONADOTROPIN AS AN IMMUNE-POTENTIATING ANTIVIRAL AGENT

This is a Provisional of U.S. application Ser. No. 60/000, 946, filed Jul. 7, 1995, and a CIP of U.S. application Ser. No. 08/338,166, filed Nov. 10, 1994, now U.S. Pat. No. 5,700,781, which is a CIP of U.S. application Ser. No. 08/318,909, filed Oct. 14, 1994, abandoned.

BACKGROUND OF THE INVENTION

The present invention relates to the therapeutic application of human chorionic gonadotropin (HCG) for its previously unappreciated, immune-potentiating properties in human patients. More specifically, the present invention relates to the use of HCG in treatment of and prophylactic intervention against a variety of viral infections, including but not limited to those associated with the Acquired Immune Deficiency Syndrome (AIDS).

HCG is a water-soluble glycoprotein hormone which is produced by the human placenta and excreted in urine from pregnant women, with the highest levels observed during the first trimester of pregnancy. HCG is detectable in both the serum and the urine of pregnant women, and otherwise in no other human serum or urine, with rare exceptions. Relatively rare germ cell malignancies of the testes produce HCG, and patients with common lung and pancreatic cancers, inter alia, have detectable HCG serum levels in very rare instances.

HCG is composed of two polypeptide chains, α and β. The α chain is identical to the α chains of luteinizing hormone (LH), follicle stimulating hormone (FSH) and thyroid stimulating hormone (TSH). The β subunit of HCG is closest in structure to the β subunit of LH (85% homology), and is 35% homologous to the FSH β chain HCG is prepared for intramuscular injection as a sterile lyophilized powder. HCG is marketed by Serono, Inc. (PROFASI™) in vials containing either 5,000 or 10,000 USP Units. It also is sold by Wyeth-Ayerst (PREGNYL™) and Schein Laboratories (GOLDLINE™). The gene for HCG has been cloned, see Fiddes & Goodman, *Nature* 281: 351–56 (1979), but recombinant HCG is not yet available commercially.

An HCG-mediated regression of Kaposi's sarcoma (KS) has been documented in nude (immunodeficient) mice in which tumors have been induced by inoculation with a tumor cell line, KS Y-1, derived from human KS. See Gallo in TENTH INTERNATIONAL CONFERENCE ON AIDS, Volume 2 (proceedings of meeting in Yokohama, Japan, on Aug. 7–12, 1994; hereafter "Yokohama AIDS Conference Proceedings"). In this regard, the affected nude mice received intramuscular administration of 50,000 to 100,000 International Units (IU) of HCG per 10 grams body weight, three times a week. It also was noted that KS Y-1 did not induce tumor development in female mice during pregnancy, while non-pregnant mice developed massive KS. See *Japan Science Scan,* Aug. 15, 1994.

A unified perspective on these observations was not immediately evident, and broader implications for therapeutic application were not elaborated. The present inventor realized, however, that transmission of HIV from infected mothers to their fetuses rarely if ever occurs during the first, second, or third trimesters of pregnancy. Blanche in Yokohama AIDS Conference Proceedings (Plenary Session 11); DeRossi et al., *AIDS* 10: 1117–20 (1992). In this context, the inventor perceived the significance of the fact that the only natural state in which HCG is markedly elevated in human serum is during pregnancy, when FSH and LH are suppressed completely to allow the corpus luteum to secrete progesterone and estrogen. Thus, only after the placenta decreases its production of HCG and is delivered, and the mother and baby experience a massive drop in HCG, can the baby acquire HIV from maternal blood or from nursing.

SUMMARY OF THE INVENTION

In light of these and other considerations, it has been discovered by the inventor that administration of HCG to human patients has an immune-potentiating effect which is manifested, pursuant to one aspect of the present invention, in a broad spectrum anti-viral activity. Accordingly, the present invention contemplates (A) administering to a subject an amount of HCG that is clinically effective in treating or preventing a viral infection which the subject suffers or is at risk for suffering, and then (B) monitoring the subject for parameters of the infection, thereby to gauge the efficacy or progress of the treatment. Illustrative viruses against which the invention can be applied are HIV, cytomegalovirus (CMV), a KS-producing herpes virus, and a virus of the genus Molluscipoxvirus, among other viruses.

Pursuant to a preferred embodiment of the invention, the effective amount of HCG thus administered is such as to produce a circulating concentration of HCG sufficient to suppress LH totally. According to another preferred embodiment, the effective amount is administered, three times a week, in a dosage ranging between about 4,000 and 20,000 IU. In accordance with yet another preferred embodiment, the effective amount is such as to produce an elevation in $T_8$ count or $T_4$ count of at least about 10% over pre-treatment levels in the subject after one month of therapy.

Treatment according to the present invention can be effected when the subject is a neonate and step (A) is carried out at delivery. In addition, step (A) may be effected after delivery, until the immune system of said neonate matures.

In accordance with another aspect of the present invention, HCG is provided in a therapeutic, sustained-release form which is particularly well-suited for implementing the aforementioned therapy.

DETAILED DESCRIPTION OF PREFERRED EMBODIMENTS

A key aspect of the present invention is the inventor's insight that exogenous HCG potentiates or intensifies the effectiveness of the immune system. This "immune-potentiating" capability of HCG can be exploited to therapeutic advantage in a number of specific ways which are illustrated in the following sections.

In general terms, the design of a therapeutic protocol within this invention is guided by the observations that HIV is not transmitted from mother to fetus throughout pregnancy, that maternal FSH and LH levels fall to zero, and that HCG is produced by the placenta. HCG is detectable in female urine within days of conception; levels rise to between about 10,000 and 300,000 IU per liter of blood during the next six months of gestation. At delivery, with placental delivery HCG levels drop to zero, and the baby is susceptible to HIV infection from the mother at delivery and at breast feeding. The present inventor surmised from this that levels of HCG sufficient to completely suppress LH are needed to prevent HIV transmission from mother to child. Based on this insight, the inventor also recognized that administering exogenous HCG to achieve blood levels of the hormone sufficient to suppress LH totally likewise would decrease viral load and reconstitute the immune system of individuals already infected, as well as prevent against HIV and other viral infections. By the same token, exogenous HCG administration at doses adequate to cause complete suppression of LH and FSH would have an immune-potentiating effect generally, thereby helping to fight a range of infections and to correct immune disturbances in patients suffering from a diversity of disorders, ranging from cancer to autoimmune diseases.

In this regard, the present inventor found that administration of HCG to HIV-infected people raises $CD_8$ T-cell ($T_8$ cell) counts. This effect is extremely important because $T_8$ cells are needed to produce a cytokine that further blocks HIV replication. Moreover, a $CD_8$ cytokine is needed for development of $CD_4$ T-cells ($T_4$ cells). See Levy in Yokohama AIDS Conference Proceedings. After $T_4$ cells increase, they can produce larger quantities of a cytokine, interleukin-1, which in sufficient amounts then increases production of $T_8$ cells. Thus, HCG causes a $T_8$ elevation that engenders a self-perpetuating cycle, in which a $T_8$ cell product encourages $T_4$ proliferation and a $T_4$ cell product fosters $T_8$ production.

Via this cycle, the administration of HCG corrects a basic thymic disturbance in AIDS, which is widely acknowledged to be a result of HIV infection. In addition, HCG influences monocyte production of interleukin-10 and, in turn, interleukin-6 and tumor necrosis factor. See Fauci, ibid.

There also are indications that HCG binds the thymus, through which early lymphocytes traffic repeatedly, losing and acquiring various T-cell antigens until, in a final passage when both $T_4$ and $T_8$ markers are present initially, the cells lose one or the other marker and become committed to $T_4$ or $T_8$ cells. A first indication in this regard is that the thymus is largest in the newborn, when HCG still is present, and involutes during childhood. As second indication is that T-cell-mediated autoimmune diseases such as myasthenia gravis and aplastic anemia, which often are treated via thymectomy, have been reported to go into remission with pregnancy, when HCG levels are high.

HIV may be tropic to the thymus, and HIV infection of the thymus de novo may perturb the regulation of $T_4$ and $T_8$ antigenic markers as T-cells make their final passages through the thymus. Harris, *Medical Hypothesis* 36: 379–80 (1991). From the perspective of HCG activity, it is notable that T-cell leukemias now are classified routinely in terms of maturation arrest at various stages of T-cell development in the thymus. By the same token, HIV infection in hematological terms is an aleukemic leukemia of T-cells which develops only after HCG disappears and the thymus involutes. In the face of a deleterious viral infection, therefore, administration of HCG in accordance with the present invention could cause a resurgence of thymic function and counteract the loss of $T_4$ and $T_8$ cells occasioned by the HIV infection.

Administration of HCG may have a direct antiviral effect, moreover, by virtue of the ability of the hormone to inhibit reverse transcriptase. Bourinbaiar & Nagorry, *FEMS Microbiol. Lett.* 96: 27–30 (1992). When a reverse transcriptase is inhibited, viral RNA is no longer able to copy itself into DNA and integrate itself into the genome of the infected subject. Similarly, HCG could inhibit the reverse transcriptase enzyme of other retroviruses as well, inhibiting their propagation. Examples of such viruses include human T-cell leukemia virus I (HTLV-I), which is endogenous to the Caribbean and to Israel, and human T-cell leukemia virus III (HTLV-III), which causes hairy cell leukemia.

Additionally, HCG may act like Peptide T, an octapeptide that blocks the gp-120 receptor for HIV on T-cells and neuronal cells. See Pert et al., *Psychopharmacol. Bull.* 24: 315–19 (1988). Like HCG, Peptide T raises testosterone levels. Harris, *AIDS Patient Care*, Volume 6 (February, 1992).

By whatever mechanism or mechanisms, in any event, a therapeutic approach according to the present invention does potentiate the patient's immune system to substantial and unexpected advantage. For example, administration of HCG according to the present invention is shown to effect an increase in T cell levels in HIV-positive patients, initially for $T_8$ cells and thereafter for $T_4$ cells as well, as discussed below in Section I. A continuation of the HCG therapy at 4,000 IU doses, administered systemically (e.g., intramuscularly) over a period of months, three times per week (for example, on every Monday, Wednesday, and Friday), results for most patients in increases each month in both $T_8$ and $T_4$ counts, along with an ongoing improvement in patient well-being. (Higher doses may be needed in some patients to suppress LH totally and achieve maximum efficacy; see below.) As a further indication of immune potentiation in this regard, patients receiving such HCG therapy also experience freedom from or, if already infected, remission of symptoms associated with opportunistic infections by other, non-viral pathogens responsible, for example, for pneumocystis pneumonia, encephalitis caused by toxoplasmosis, Cryptosporidia colitis, candidal stomatitis, histoplasmosis, and *Mycobacterium tuberculosis*.

For certain patients, higher levels of HCG may be needed in carrying out the present invention. Blood levels of LH are virtually zero in pregnancy, and are usually suppressed significantly in non-pregnant, HIV-positive patients. The inventor has observed, however, that HIV-positive patients with upper normal or high levels of LH require higher doses of HCG to suppress LH fully and "imitate" the condition of pregnancy, as discussed above. Complete suppression of LH levels is believed to be necessary to achieve maximum therapeutic effect by HCG, since LH and HCG compete for receptors on relevant cells.

Also, because HCG directly suppresses KS tumor survival and growth, patients with KS require higher doses of HCG to control both KS and HIV. Thus, a patient with both KS and HIV has one "sink" (KS tumor) which takes up a large portion of HCG and which must be saturated before the second sink (HIV) can be accommodated effectively. Likewise, the presence in a patient of other, concomitant viral infections or other immune problems would represent further HCG sinks and, hence, would have to be considered in adjusting HCG dosage upward for optimal treatment of an infection of primary interest, such as HIV.

Other variables will impact upon the essentially empirical endeavor of optimizing HCG dosage in the present invention. It is a basic tenet of endocrinology, for example, that there is individual variation as to the respective quantities of particular receptors on their cells. In addition, individuals will differ in the avidity and affinity of particular receptors for the cognate hormone, and these binding characteristics may change over the course of therapy. Accordingly, it is an aspect of the present invention that HCG and LH blood levels are monitored, in conjunction with the observed indicia of the infection being treated as well as of other HCG sinks, to the end of maintaining HCG blood levels at least in the range of those seen in pregnant women, i.e., from detectable levels to about 300,000 IU, while causing normal levels of free testosterone, estradiol, and progesterone. Ongoing measurement of hormonal levels can be accomplished via conventional methodology described, for example, by Brody and Carlstrom, *J. Clin. Endocrinol.* 22: 564–74 (1962).

The inventor also has determined that an interruption of therapy or a decrease in HCG dosage results in a decline in T cell counts and clinical status. Accordingly, longer term administration of HCG, continuing for months or even years, is preferred.

To this end, and to allow for adjustments needed to achieve and maintain the in vivo levels of HCG that characterize the present invention, the hormone can be administered intramuscularly but not without the technical difficulties associated with multiple injections. For greater control and ease of long-term administration of HCG, therefore, the use of HCG in a sustained-release modality represents a more preferred approach.

One sustained-release form of HCG is a transdermal HCG patch, after the fashion of the DURAGESIC™ fentanyl patch. In this context, transdermal delivery of proteins like HCG has been accomplished iontophoretically or electroosmotically, i.e., under the influence of an electric field. See, for example, U.S. Pat. No. 4,878,892, No. 4,940,456, No. 5,032,109, No. 5,158,537 and No. 5,250,023. The respective contents of these documents, as well as of the other publications cited in the present specification, are hereby incorporated by reference.

Another sustained-release form of HCG within the present invention is an implantable HCG delivery system. In the manner of the NORPLANT™ levonorgestrel implant, a type of device in this category employs passive release of HCG through a non-biodegradable, rate-limiting membrane element composed, for instance, of a hydrogel or a microporous polymer. See U.S. Pat. No. 5,292,515 and patent documents cited there, such as U.S. Pat. No. 3,993,072, and U.S. Pat. No. 4,959,217. Another type of HCG implant contemplated by the present invention incorporates a pump function to administer the hormone. See, for instance, U.S. Pat. No. 5,030,216, No. 5,368,588, No. 5,370,635 and No. 5,391,164. The pumping action can be osmotically driven or patient-activated, for example, or can be controlled by a servomechanism which allows for the "titration" of hormone and, hence, dosage adjustment in light of monitored parameters, such as HCG and LH blood levels and the clinical symptoms of the condition under treatment.

Since the α chains of HCG, LH and FSH are identical, it is the β subunit of HCG that gives the hormone its specificity. It is expected, therefore, that an HCG β-chain polypeptide will have the immune-potentiating activity of the hormone itself and, hence, that the term "HCG" herein can apply to the hormone and the polypeptide alike.

Knowledge of the structure of the HCG β chain also should permit the production of variants of HCG, such as an HCG homolog with intra-sequence substitutions, relative to the native hormone sequence, and mimetics of HCG. Mimetics are peptide-containing molecules which mimic elements of protein secondary structure. See, for example, Johnson et al. in BIOTECHNOLOGY AND PHARMACY (Chapman and Hall, 1993). The underlying rationale behind the design of such mimetics is that the peptide backbone of the native protein (here, HCG) exists chiefly to orient amino acid side chains in such a way as to facilitate molecular interactions, such as those between the hormone and its receptor(s). See Morgan et al., *Ann. Rep. Medicinal Chem.* 1989: 243.

I. Therapy Directed Against HIV Infection

A preferred embodiment of the present invention entails administration of HCG to ameliorate the impact of HIV infection per se. As noted, AIDS is widely acknowledged to be a result of such infection.

The present inventor and others had observed that primary anterior pituitary insufficiency is common in HIV-infected patients. Thus, the relevant literature described low levels of thyroxine secondary to low levels of thyroid stimulating hormone, low levels of cortisol secondary to low levels of adrenocorticotropin hormone, and low levels of testosterone secondary to low levels of luteinizing hormone.

It was difficult to determine the exact frequency of these endocrine disorders in HIV-infected patients, due to the complexity of their overall disease processes, and precise statistics have been unavailable on how many HIV-infected patients suffered hypogonadotrophic hypogonadism, a condition marked by low free-serum testosterone and inappropriately low LH levels (see below for discussion of other clinical criteria). In the inventor's experience, however, hypogonadotrophic hypogonadism is common in terminal AIDS patients and often can be seen early in HIV infection, when usual clinical and laboratory workup suggest that the patient is otherwise well.

In view of these considerations, the present inventor elected to treat several HIV-positive patients who also had hypogonadotrophic hypogonadism with HCG, thereby to demonstrate the clinical benefits of HCG beyond those predicted by correcting hypogonadism. Patients were deemed to be clinically hypogonadal if they met both major criteria of hypogonadism—loss of libido and a decreased ability to achieve normal erections—and at least two of six "minor" criteria: (1) decreased beard growth; (2) loss of masculine lean muscle mass with either wasting or development of a more typically female habitus, with an increased ratio of fat to muscle; (3) presence of female pattern pubic hair distribution (triangular-shaped) as opposed to male pattern pubic hair distribution (diamond shaped); (4) change in voice characteristics with loss of ability to reach lower notes; (5) change in personality with loss of typical male assertiveness/aggression, taking into account personality changes which could be attributed to drug therapy, dementia, and the physical and psychological consequences of coping with HIV; and (6) change in normal dreaming with loss of dreams about sex. All patients who met these clinical criteria were then evaluated by standard laboratory criteria. Hypogonadotrophic hypogonadism was diagnosed if the patients had a low serum free testosterone for their decade of life with a frankly low or inappropriately normal level of luteinizing hormone and follicle stimulating hormone.

HCG was administered from two sources. PROFASI™ was obtained from Serono Laboratories in vials of 10,000 international units (IU) per vial, and generic HCG was obtained from Goldline/Schein Pharmaceuticals in vials of 10,000 IU per vial. Each 10,000 IU vial was reconstituted with 0.75 cc of bacteriostatic water for HCG intramuscular (IM) administration. HCG was administered according to the FDA-approved protocol for treatment of hypogonadotrophic hypogonadism.

HCG initially was administered at 1,000 IU IM, three times per week, for three weeks. The regimen thereafter involved 1,000 IU IM twice a week for three weeks, followed by 4,000 IU IM three times per week for several months. In all, thirty HIV-positive patients were treated with HCG.

Patients were started on HCG therapy within the present invention at various points of time. Day one of therapy varied by months between patients. Thirty percent (30%) of the patients reported an initial but transient increase in emotional lability, mood swings, and aggressiveness. After four weeks on therapy, 90% of the patients reported increased appetite, sometimes, but not always, accompanied by specific food cravings, increased lean muscle mass, weight gain, increased strength, increased libido, and increased number and intensity of spontaneous erections. Sixty-five percent noted an increase in the volume of their ejaculate. Ninety-six percent reported stabilization or an increase in secondary sex characteristics, including increased hirsutism and increased muscularity. Seventy-five percent of patients reported acne forme eruptions during the first month of therapy. Thirty percent of patients reported decrease in the tenor of their voices. Seventy percent of patients noted transient nipple tenderness and areolar growth. Seven percent noted transient galactorrhea. By week four, fifty percent of patients reported improved neurocognitive skills. Twelve percent reported improved facial skin appearance simulating "a glow of pregnancy" (this was particularly evident in African-Americans). Patient 21 showed facial changes typical of the trial group. Regression of molluscum contagiosum (see Section III, infra) was documented in the 12% of the patients in whom it had been previously diagnosed.

Toxicity was reported as insignificant. Seven percent had gastrointestinal side-effects. One patient complained of nausea and frontal headache 24 hours after each injection. Another patient complained of nausea and diarrhea four to six hours after each injection. Side effects dissipated over time. No patient complained of excessive pain at sites of IM injections. Fifty percent of the patients complained of having to visit our medical facility three times per week. This was remedied by teaching patients to self-administer HCG. No patient reported problems related to hepatic function, and there was no worsening of liver function tests. No prostatic abnormalities were noted on physical exam or on laboratory analysis. All patients noted increased rate of fingernail and toenail growth. Several patients noted new hair growth in areas of male pattern baldness. No patient's testosterone rose above the acceptable levels for his age group. All patients' free testosterone levels normalized by the fourth week of therapy.

T-cell counts measured just before initiation of therapy and one month later evidenced a favorable trend (see Tables 1 and 2). $T_4$ cells rose an average of 21.04 $T_4$ cells per cubic millimeter, or 10.55%. $T_8$ cells rose an average of 104.96 cells per cubic millimeter or 15.59%. Patients whose $T_4$ counts were equal to or above 200 cells per cubic millimeter at initiation of therapy were studied as a separate subset. Twelve of the 26 patients began HCG when their $T_4$ cells were greater than 200 cells per cubic millimeter (range 202–797). In this subgroup, $T_4$ counts rose an average of 43.67 cells per cubic millimeter or 12.64% and $T_8$ cells rose an average of 108.58 cells per cubic millimeter or 13.79%. Fourteen patients $T_4$ cells increased or stabilized and twelve patients $T_4$ cells decreased. We had expected that patients with greater than 200 $T_4$ cells/mm$^3$ at baseline would benefit most greatly. Four patients with less than 200 $T_4$ cells/mm$^3$ (patients 13, 17, 19 and 23) showed significant increases in $T_4$ cells, however, and three patients with greater than 200 $T_4$ cells/mm$^3$ (patients 2, 15 and 22) showed decreases in $T_4$ cells.

TABLE 1

$T_4$ Cell Changes Before Initiation of Therapy and 1 Month Later

| | Time 1 cells/mm$^3$ | Time 2 cells/mm$^3$ | Actual Changes | % change between times |
|---|---|---|---|---|
| 1) | 103.00 | 90.00 | 13.00− | 12.62%− |
| 2)* | 405.00 | 335.00 | 70.00− | 17.28%− |
| 3) | 50.00 | 47.00 | 3.00− | 6.00%− |
| 4) | 14.00 | 6.00 | 8.00− | 57.14%− |
| 5)* | 225.00 | 225.00 | NC | NC |
| 6) | 152.00 | 99.00 | 53.00− | 34.87%− |
| 7) | 29.00 | 25.00 | 4.00− | 13.79%− |
| 8)* | 797.00 | 880.00 | 83.00+ | 10.41%+ |
| 9)* | 282.00 | 346.00 | 64.00+ | 22.70%+ |
| 10) | 77.00 | 72.00 | 5.00− | 6.49%− |
| 11)* | 336.00 | 554.00 | 218.00+ | 64.88%+ |
| 12)* | 228.00 | 448.00 | 220.00+ | 96.49%+ |
| 13) | 147.00 | 197.00 | 50.00+ | 34.01%+ |
| 14)* | 242.00 | 246.00 | 4.00+ | 1.65%+ |
| 15)* | 302.00 | 208.00 | 94.00− | 31.13%− |
| 16) | 73.00 | 52.00 | 21.00− | 28.77%− |
| 17) | 193.00 | 213.00 | 20.00+ | 10.36%+ |
| 18) | 5.00 | 3.00 | 2.00− | 140.00%− |
| 19) | 93.00 | 157.00 | 64.00+ | 68.81%+ |
| 20)* | 444.00 | 468.00 | 24.00+ | 5.41%+ |
| 21) | 53.00 | 64.00 | 11.00+ | 20.75%+ |
| 22)* | 332.00 | 282.00 | 50.00− | 15.06%− |
| 23) | 2.00 | 4.00 | 2.00+ | 100.00%+ |
| 24)* | 349.00 | 456.00 | 107.00+ | 30.66%+ |
| 25) | 50.00 | 35.00 | 15.00− | 30.00%− |
| 26)* | 202.00 | 220.00 | 18.00+ | 8.91%+ |
| Subtotal | 5185.00 | 5732.00 | 547.00+ | 10.55%+ |
| Avg. (26) | 199.42 | 220.46 | 21.04+ | |
| *Subtotal | 4144.00 | 4668.00 | 524.00+ | 12.64%+ |
| Avg. (12) | 345.33 | 389.00 | 43.67+ | |

*Indicates initial $T_4$ cell count greater than 200 cells per cubic millimeter.

TABLE 2

$T_8$ Cell Changes Before Initiation of Therapy and 1 Month Later

| | Time 1 cells/mm$^3$ | Time 2 cells/mm$^3$ | Actual Changes | % change between times |
|---|---|---|---|---|
| 1) | 410.00 | 477.00 | 67.00+ | 16.34%+ |
| 2)* | 1162.00 | 1131.00 | 31.00− | 2.67%− |
| 3) | 986.00 | 1043.00 | 57.00+ | 5.78%+ |
| 4) | 501.00 | 294.00 | 207.00− | 41.32%− |
| 5)* | 797.00 | 943.00 | 146.00+ | 18.32%+ |
| 6) | 514.00 | 312.00 | 202.00− | 39.30%− |
| 7) | 748.00 | 665.00 | 83.00− | 11.10%− |
| 8)* | 617.00 | 575.00 | 42.00− | 6.81%− |
| 9)* | 850.00 | 998.00 | 148.00+ | 17.41%+ |
| 10) | 491.00 | 1013.00 | 522.00+ | 106.31%+ |
| 11)* | 777.00 | 1245.00 | 468.00+ | 60.23%+ |
| 12)* | 660.00 | 1169.00 | 509.00+ | 77.12%+ |
| 13) | 493.00 | 1123.00 | 630.00+ | 127.79%+ |
| 14)* | 555.00 | 485.00 | 70.00− | 12.61%− |
| 15)* | 725.00 | 497.00 | 228.00− | 31.45%− |
| 16) | 1951.00 | 1551.00 | 400.00− | 20.50%− |
| 17) | 431.00 | 620.00 | 189.00+ | 43.85%+ |
| 18) | 31.00 | 21.00 | 10.00− | 32.25%− |
| 19) | 621.00 | 1297.00 | 676.00+ | 108.86%+ |
| 20)* | 897.00 | 892.00 | 5.00− | .56%− |
| 21) | 64.00 | 105.00 | 41.00+ | 64.06%+ |
| 22)* | 846.00 | 850.00 | 4.00+ | .47%+ |
| 23) | 390.00 | 616.00 | 226.00+ | 57.95%+ |
| 24)* | 463.00 | 684.00 | 221.00+ | 47.73%+ |
| 25) | 426.00 | 346.00 | 80.00− | 18.78%− |
| 26)* | 1101.00 | 1284.00 | 183.00+ | 16.62%+ |
| Subtotal | 17507.00 | 20236.00 | 2729.00+ | 15.59%+ |
| Avg. (26) | 673.35 | 778.31 | 104.96+ | |
| *Subtotal | 9480.00 | 10753.00 | 1303.00+ | 13.79%+ |
| Avg. (12) | 787.50 | 896.08 | 108.58+ | |

*Indicates initial $T_4$ cell count greater than 200 cells per cubic millimeter.

Eight of the original 26 patients were evaluated when they completed five months of HCG therapy within the present invention. (The remaining 18 patients still were receiving drug but had not yet received a full five months of therapy.) $T_4$ counts measured after five months of treatment rose an average of 59.38 cells per cubic millimeter, or 17.78%, from levels after one month of therapy (see Table 3). $T_8$ counts rose an average of 377.13 cells per cubic millimeter, or 43.35% (Table 4). Seven patients showed a significant increase in $T_4$ counts, and one patient showed an insignificant drop in $T_4$ counts. The three patients with less that 200 $T_4$ cells/mm$^3$ (patients 1, 3 and 13) showed increases in $T_4$ counts. Four of the five patients with $T_4$ counts greater than 200 $T_4$ cells/mm$^3$ (patients 8, 14, 24 and 26) showed increases in $T_4$ counts. The remaining patient with a $T_4$ count greater than 200 cells/mm$^3$ (patient 20) showed an insignificant decrease in $T_4$ counts. $T_8$ counts rose in all patients by month five.

These data indicate that essentially all patients, regardless of initial $T_4$ counts, eventually showed increases in $T_4$s and $T_8$s. This conclusion was born out in subsequent patient questionnaires, which generally reflected increasing $T_8$ and $T_4$ counts over time, as well as increased well-being.

TABLE 3

$T_4$ Cell Changes After 1 Month of Therapy and After 5 Months of Therapy

|   | Time 2 cells/mm$^3$ | Time 3 cells/mm$^3$ | Actual Changes | % change between times |
|---|---|---|---|---|
| 1) | 90.00 | 106.00 | 16.00+ | 17.77%+ |
| 3) | 47.00 | 96.00 | 49.00+ | 104.26%+ |
| 8) | 880.00 | 1054.00 | 174.00+ | 19.77%+ |
| 13) | 197.00 | 260.00 | 63.00+ | 31.98%+ |
| 14) | 246.00 | 275.00 | 29.00+ | 11.18%+ |
| 20) | 468.00 | 466.00 | 2.00− | .43%− |
| 24) | 456.00 | 514.00 | 58.00+ | 12.72%+ |
| 26) | 288.00 | 376.00 | 88.00+ | 30.56%+ |
| Subtotal | 2672.00 | 3147.00 | 475.00+ | 17.78%+ |
| Avg. | 334.00 | 393.38 | 595.38+ | |

TABLE 4

$T_8$ Cell Changes After 1 Month of Therapy and After 5 Months of Therapy

|   | Time 2 cells/mm$^3$ | Time 3 cells/mm$^3$ | Actual Changes | % change between times |
|---|---|---|---|---|
| 1) | 477.00 | 536.00 | 599.00+ | 12.37%+ |
| 3) | 1043.00 | 2341.00 | 1298.00+ | 124.44%+ |
| 8) | 575.00 | 967.00 | 392.00+ | 68.17%+ |
| 13) | 1123.00 | 1235.00 | 112.00+ | 9.97%++ |
| 14) | 485.00 | 752.00 | 267.00+ | 55.05%+ |
| 20) | 892.00 | 932.00 | 40.00+ | 4.48%+ |
| 24) | 684.00 | 929.00 | 245.00+ | 35.82%+ |
| 26) | 1680.00 | 2284.00 | 604.00+ | 35.95%+ |
| Subtotal | 6959.00 | 9976.00 | 3017.00+ | 43.35%+ |
| Avg. | 869.88 | 1247.00 | 377.13+ | |

The fact that $T_4$ and $T_8$ counts progressively rose, and the fact that no patient receiving HCG has had an intercurrent infection necessitating hospitalization, are persuasive indicators of the antiviral efficacy of an HCG-based, immune-potentiating therapy according to the present invention. It is noteworthy in this regard that three patients who did not meet criteria for hypogonadotrophic hypogonadism nevertheless benefitted from the above-described treatment. These three patients had a decrease in anorexia, increase in appetite, increase in energy, and increase in strength. Testosterone levels remained within the normal range but FSH and LH levels were decreased. Increased rate of nail growth and improved neurocognitive skills were universal. Two patients suffering from molluscum contagiosum reported its regression. All three had significant progressive elevations in $T_4$ and $T_8$ counts.

The observation that $T_4$ cells rose over time as $T_8$ cells rose over time indicates that HCG impacts on $T_4$ cells and $T_8$ cells concurrently. Time until HCG raises $T_4$ and $T_8$ counts in individual patients is not totally predictable but may reflect a change in the natural history of HIV in each particular patient.

A continuing therapeutic program conducted by the inventor along the foregoing lines has resulted in forty-one patients' receiving at least five months of therapy according to the present invention. Thirty-eight of these patients (93%) show consistent, progressive elevations of $T_8$ and $T_4$ counts, and none of the 38 have had an intercurrent infection. Three patients who were comparatively non-responsive were the only ones whose LH levels had not been suppressed totally. Increasing the HCG dosage of IM injections to 20,000 IU for these patients has resulted in LH suppression and subsequent increases in $T_4$ and $T_8$ counts.

In the context of anti-HIV therapy, the present invention offers several advantages over conventional approaches. Unlike therapy with currently prescribed reverse transcriptase inhibitors (zidovudine, dideoxyinosine, dideoxycytidine, 2,3-didehydro-3-deoxythymidine and Lamivudine (GR109714X)), secondary toxicity such as anemia, neutropenia, myopathy, pancreatitis, diarrhea, and neuropathy did not occur. Unlike interleukin-2 therapy, T cells did not rise and fall but continued an upward progression. No drug resistance relating to HCG has emerged, in contrast to therapies based on reverse transcriptase inhibitors and protease inhibitors. Toxicity was very low and side-effects were generally beneficial.

HCG also compares favorably with other drugs employed only to improve diminished quality of life. As an appetite stimulant, for example, HCG is as effective as megestrol, which primarily causes fat gain, and is more effective than dronabinol, which is associated with dysphoria.

II. Therapy Against Kaposi's Sarcoma

Another preferred embodiment of the present invention is directed to treating KS via administration of HCG. A rare neoplasm prior to the AIDS epidemic, KS today is the most prevalent neoplasm of HIV-infected individuals. See, for example, Lilenbaum et al., *AIDS* 8: 141 (1994), and Stein et al., *Israel J. Med. Sci.* 30: 298 (1994).

KS associated with AIDS consists of neo-angiogenesis and dysplastic hyperplasia of endothelial cells. It generally presents as individual placque-like cutaneous tumors, often at the tips of the nose and ear lobes. Although often behaving like a late-opportunistic infection, it may present early in HIV infection even when the $T_4$ count is relatively high. When it spreads to visceral organs, such as lung parenchyma, prognosis for life is generally three months.

The etiology of AIDS-associated KS has been the subject of controversy. Very recent reports suggest, however, that AIDS-associated KS is a consequence of infection with herpes virus. Ninety percent of KS and 15% of non-KS tissues in HIV-infected individuals contained DNA sequences homologous with genes of the capsid and tegument proteins of *Herpes viridae* spp. *saimiri* and Epstein-Barr DNA viruses. See Chang et al., *Science* 266: 1865 (1994); Ambroziak et al., *Science*, 268: 582 (1995); Moore et al., *N. Eng. J. Med.* 332: 1181 (1995); Cesarman et al., loc. cit.: 1186.

To demonstrate the impact of HCG's immune-potentiating capability in this context, six HIV-positive patients were selected who were suffering from KS. Pursuant to a preferred embodiment of the present invention, a level of HCG administration in the range of 150,000 to 700,000 IU for an average 70 kilogram man, three times a week, was identified. The inventor dose-escalated over the first three to five weeks, until it became clear that patients could tolerate rapid escalation of doses of HCG to 700,000 IU, three times a week. Serum HCG levels were measured, and they fell within the range for pregnancy. Thus, levels from 1,303 to 7,514 MIU/ml serum were documented.

All patients underwent biopsy of appropriate lesions, and all patients were considered evaluable. Responses to HCG were considered clinical complete, clinical partial, stable, or progressed as defined by Krown et al., *J. Clin. Oncol.* 7: 1201–07 (1989). As for the protocol described in Section I above, PROFASI™ HCG was obtained from Serono Laboratories, and Goldline HCG from Schein Pharmaceuticals.

KS lesions were assessed every two weeks or sooner, if changes were dramatic in less than two weeks. Assessment consisted of counting numbers of lesions, notation of changes in individual lesions (i.e., flattening of nodular lesions to form macules or decrease in purple pigmentation), description of new lesions, photographs of lesions, and measurements of lesions assessed by the sum of the longest perpendicular dimensions of five index lesions (or all lesions if less than five were originally documented), and notation of edema around lesions or presence of effusions.

All six of the patients studied showed marked and consistent regression in their Kaposi's burden. Furthermore, all patients reported an improved quality of life (see Table 5). Karnofsky performance scale improved by at least 30% in all patients. KS patients experienced total regression of molluscum contagiosum if it was present at initiation of HCG. Patients complained only of local pain at sites of multiple injections and a mild sensation of skin tightening.

Improvements in immunologic markers in these patients were less consistent than those seen in patients given lower doses of HCG for hypogonadotrophic hypogonadism. Although the KS patients received 80%–160% more HCG than hypogonadal, HIV-positive patients without KS, and although their HCG levels consistently increased, serum-free testosterone levels consistently increased, FSH and LH levels consistently decreased, and serum-free testosterone levels consistently increased. Data on $T_4$ cells, $T_8$ cells and HIV P-24 antigen were inconsistent (see Table 6).

TABLE 5

Quality of Life in Kaposi's Patients on High Dose HCG

| PATIENT | Energy Level[1]: | Appetite[2]: | Weight-Change in lbs.[3]: | Mood Change[4]: | Cognitive Skills[5]: |
|---|---|---|---|---|---|
| ONE | 2 → 5 | 1 → 5 | 141 → 147 | 1 → 5 | 1 → 4 |
| TWO | 2 → 3 | 2 → 3 | 155 → 155 | 2 → 5 | 4 → 5 |
| THREE | 4 → 5 | 3 → 5 | 141 → 150 | 4 → 5 | 4 → 4 |
| FOUR | 3 → 5 | 3 → 5 | 151 → 156 | 4 → 5 | 4 → 5 |
| FIVE | 1 → 3 | 1 → 3 | 168 → 170 | 1 → 4 | 2 → 4 |
| SIX | 2 → ? | 1 → 3 | 145 → 151 | 3 → 5 | 4 → 5 |

[1] - Bedridden
2 - Self care
3 - Work 4 hrs. a day
4 - Work 8 hrs. a day
5 - Normal lifestyle
[2] 1 - Anorexia
2 - Minimal oral intake
3 - Moderate decrease
4 - Normal appetite
5 - Increased appetite
[3] Weight gain accompanied by increased muscle mass and decreased adipose tissue.
[4] 1 - Very depressed
2 - Moderately depressed
3 - Pessimistic
4 - "Realistic"
5 - Optimistic
[5] 1 - Demented
2 - Often confused and forgetful
3 - Occasionally confused and forgetful
4 - Rarely confused and forgetful
5 - Normal

TABLE 6

CHANGES IN HORMONAL AND IMMUNOLOGIC MARKERS IN KAPOSI'S PATIENTS BEFORE AND AFTER SEVERAL TREATMENTS WITH HIGH DOSE HCG (Normal levels shown below[1].)

| Baseline for: | Patient 1 | Patient 2 | Patient 3 | Patient 4 | Patient 5 | Patient 6 |
|---|---|---|---|---|---|---|
| HCG MIU/ml | <2 | <2 | <2 | <2 | <2 | <2 |
| $T_4$ cells/mm$^3$ | 442 | 4 | 140 | 20 | 59 | 56 |
| $T_8$ cells/mm$^3$ | 949 | 737 | 465 | 987 | 970 | 546 |
| Beta-2 microglob mg/l | 3.3 | 4.5 | 2.6 | 4.3 | 3.6 | 5 |
| HIV P-24 Ag pico/ml | 242 | <2.0 | 449 | <2 | <2 | 19 |
| Free testosterone pg/ml | 22.61 | 17.8 | 16.3 | 7.68 | 5.19 | 9.14 |
| FSH/LH MIU/ml | 14.4/4.5 | 2.6/1.5 | 3.0/17.3 | 2.9/3.0 | 4.8/5.0 | 7.4/6.4 |
| | Patient 1: 1 week after starting regimen | Patient 2: 5 weeks after starting regimen | Patient 3: 4 weeks after starting regimen | Patient 4: 3 weeks after starting regimen | Patient 5: 2.5 weeks after starting regimen | Patient 6: 2 weeks after starting regimen |
| HCG MIU/ml | 1303 | 7514 | 4242 | 2778 | 7494 | 1636 |
| $T_4$ cells/mm$^3$ | N/A | 8 | 135 | 17 | 30 | 80 |

TABLE 6-continued

CHANGES IN HORMONAL AND IMMUNOLOGIC MARKERS
IN KAPOSI'S PATIENTS BEFORE AND AFTER SEVERAL TREATMENTS
WITH HIGH DOSE HCG (Normal levels shown below[1].)

| | | | | | | |
|---|---|---|---|---|---|---|
| $T_8$ cells/mm$^3$ | N/A | 1131 | 672 | 784 | 604 | 856 |
| Beta-2 microglob mg/1 | N/A | 6.5 | 3.3 | 5.2 | 4.1 | 5.4 |
| HIV P-24 Ag pico/ml | N/A | <2.0 | 168 | <2 | <2 | 145 |
| Free testosterone pg/ml | N/A | 40 | 17.71 | 40 | 18.9 | 16.08 |
| FSH/LH MIU/ml | N/A | <1/<2 | <1/<2 | <1/<2 | <.3/<.5 | <.3/<.5 |

[1]Normal values for hormonal and immunologic markers:
Normal HCG Quantatives = 0–4 MIU/mlNormal $T_4$ = 358–1500 cells/cmm
Normal $T_8$ = 111.5–727.3 cells/cmmNormal Beta-2 ≦ 2.0 mg/l
Normal HIV P-24 < 32 picograms/mlFree Testosterone = 18–40 pg/ml
Normal FSH = 2.0–15.0 MIU/ml Normal LH = 0.0–10.0 MUI/ml HCG apparently binds preferentially to KS cells in these patients. For a given patient, time until immunologic improvement and consequent antiviral activity probably depends on total KS tumor bulk, as well as on the affinity and avidity of HCG receptors on the tumor cells of that individual. Tumor bulk is assessed by the criteria of Krown et al. (1989), supra. Thus, cutaneous tumor bulk is assessed by number and perpendicular dimensions of lesions, as well as by color, nodularity, and surrounding edema. Visceral lesions are assessed by the number of lesions and by the sum of the largest perpendicular dimensions of five index lesions.

The aforementioned data strongly indicate that KS is an HCG-responsive malignancy, and that clinically effective doses of HCG, i.e., doses effective in causing tumor regression, are relatively well-tolerated. In particular, remission of KS occurred when serum levels of HCG were achieved like those seen in women during pregnancy. Improvement of KS was seen in all patients while they continued high dose HCG therapy. Conversely, progressive KS occurred when financial or other constraints necessitated drastic reductions in doses of HCG.

The advantages associated with therapy according to the present invention were several. There has been no evidence of development of a flu-like syndrome seen with α-interferon therapy, for example. Peripheral neuropathy, cardiac compromise, gastrointestinal upset, alopecia, myelosuppression, and pulmonary fibrosis associated with administration of vincristine sulfate, doxorubicin, and bleomycin sulfate also did not occur. Radiation-associated burns and secondary infections were avoided. While the potential for sterile and infectious abscesses were considered as possible complications, they did not occur. Thus, there were significantly fewer complications associated with a high-dose HCG protocol, pursuant to the present invention, than are normally associated with conventional therapy in this area.

The following, more detailed commentaries describe clinical improvements in patients treated pursuant to the present invention.

EXAMPLE 1

Patient One presented with Kaposi's sarcoma covering 70% of his skin. No visceral disease was detected. He underwent three courses of chemotherapy with very slight improvement but with significant nausea, vomiting, and malaise. He refused further chemotherapy and elected to try high dose HCG. He received 162,000 IU HCG three times per week. He met criteria for partial clinical response with a 40% decrease in the number of lesions, a 60% transformation of the remaining nodular lesions to flat, decreased pigmentation of lesions, and no evidence of new lesions. The patient declined a repeat biopsy. All lesions retracted so that the circumferences of the lesions diminished by at least 50% and central clearing was also noted. This resulted in smaller, now "bullseye"-like pale purple lesions. The skin which had previously been affected by KS, now appeared to be fibrotic, but essentially normal. Because of the manner in which KS regressed, exact measurements of the sum of the largest perpendicular dimensions of marker lesions were considered unreliable.

EXAMPLE 2

Patient Two presented with a large nodular lesion on his skin overlying his right deltoid muscle. He elected to take HCG rather than undergo radiation or chemotherapy. He received doses of 350,000 IU HCG three times per week, and after four injections, the lesion regressed and then disappeared completely. The patient was lost to follow-up but one week later returned with multiple cutaneous nodular left chest wall lesions, a new cutaneous right deltoid lesion as well as a recurrence of the old right cutaneous deltoid lesion. The patient then received 700,000 IU HCG three times per week. Partial clinical remission was documented after nine doses. One of the chest wall lesions regressed from 12 millimeters (mm)×13 mm to 5 mm×5 mm; the other regressed from 10 mm×8 mm to 4 mm×3 mm. Skin lesions on the upper extremity again became undetectable. No new KS lesions developed on his skin nor were any detected by extensive radiologic exam. No edema was noted. The patient was free of KS, i.e., he had a complete clinical remission, when he relocated and discontinued HCG. Without HCG, his Kaposi's sarcoma rapidly progressed. The patient wanted to return to our Center for further HCG therapy, but was physically unable to do so.

EXAMPLE 3

Patient Three presented with nodular and maculopapular KS lesions covering 75% of his lower extremities and several small distinct nodular lesions on his upper extremities. Multiple chemotherapeutic treatments resulted in minimal tumor regression and unacceptable toxicity. After nine weeks of HCG at doses of 700,000 IU three times a week, upper extremity lesions disappeared, lower extremity lesions flattened. He had a partial clinical remission. The patient described his lesions as "retracting and flaking off" leaving new, normal skin. Previously confluent lesions became discrete, and central clearing was noted in some lesions. Trace pedal edema was documented, but the patient attributed this fluid retention to his standing on his feet gardening for prolonged periods of time. After nine weeks of treatment, financial constraints precluded such high doses of HCG, and the patient's dose was lowered to 20,000 IU three times per week. Over the next two weeks, four new KS lesions appeared on his face; previous lesions on his upper extremities recurred and three new lesions appeared. Lower extremity lesions increased in number, size, and nodularity. Chemotherapy was re-instituted along with HCG at 20,000 IU three times per week. Facial lesions disappeared, upper extremity and lower extremity lesions progressed, albeit at a slower pace, than when he was receiving 20,000 IU HCG three times a week alone. The patient refused etoposide.

EXAMPLE 4

Patient Four presented with a single right anterior neck lesion. Treatment with 2,500 rads external beam radiation resulted in marked regression of this lesion. Over several months, however, this lesion grew to greater than its original size (see photo 1). After eight weeks of 650,000 IU of HCG three times per week, the largest perpendicular dimensions of his only lesion decreased from 25 mm×12 mm to 14 mm×4 mm. These measurements did not completely reflect disease regression as the lesion also cleared centrally with a 60% reduction in tumor mass. Partial clinical remission was achieved. The central portion of this lesion appeared slightly fibrotic but normal.

After eight weeks of this dose of HCG therapy, we were no longer able to afford full drug cost and HCG dose was lowered to 10,000 to 20,000 IU three times a week depending on weekly availability. His lesion then progressed to greater than its original dimensions and central clearing disappeared. A new 22 mm×20 mm nodular lesion appeared over the patient's left lower back, and a new 17 mm×15 mm nodular lesion appeared over his skin behind his left ear.

EXAMPLE 5

Patient five presented with a 10 mm×3 mm hard palate lesion and multiple left lung parenchymal lesions and bilateral hilar adenopathy. He elected HCG injections as primary therapy. After four weeks of 650,000 IU HCG, three times a week, the hard palate lesion became undetectable. The patient experienced an intercurrent bout of cytomegalovirus pneumonia with left pleural effusion. After two weeks of gancyclovir treatment, computer axial tomography scans showed clearing pneumonia, decreased pleural effusion, and complete disappearance of parenchymal KS. The only evidence of KS was a radio-opaque, ring-like, pleural-based lesion at the site of a previously solid lesion. He experienced a nearly complete clinical remission.

EXAMPLE 6

Patient Six presented with KS on the skin of his right temple and right ear, and on his right parietal scalp. After two weeks of 500,000 IU HCG three times a week, these lesions were unchanged. He had stable disease. When financial constraints precluded continuation of high doses of HCG, the patient received 4,000 IU HCG three times a week, and was also treated with intra-lesional vinblastine sulfate at 0.2 cc per lesion per week. He then took a one month vacation. He returned with massive otolaryngeal disease which necessitated emergency radiation therapy, leading to a partial clinical remission. One month later the patient's KS spread to involve supraclavicular, axillary, inguinal and femoral lymphatic chains and right lung parenchyma. Administration of four rapidly escalating doses of HCG on alternating days from 150,000 IU to 350,000 IU resulted in an impressive decrease in adenopathy. The patient's pulse oximeter improved from 94% to 99%; followup x-rays have not yet shown regression of lesions. He was in partial clinical remission at the time of last examination.

III. Further Antiviral Indications and Other Applications (A) Molluscum contagiosum Molluscum contagiosum is a condition characterized by multiple wart-like nodular tumors on the face, arms, back and buttocks. This infectious disease is caused by a DNA virus morphologically resembling pox viruses of the genus Molluscipoxvirus. Patients with HIV-induced disease are particularly susceptible to molluscum contagiosum lesions, which are refractory to all therapies previously described. As noted above, however, patients have been observed for whom molluscum contagiosum lesions regressed as a result of HCG therapy within the present invention, indicating an anti-Molluscipoxvirus activity for the hormone.

In accordance with the present invention, therefore, HCG will be useful in controlling molluscum, not only in AIDS patients but also in any immune-compromised patient. Illustrative of such patients are transplant recipients, individuals receiving chemotherapy, dialysis patients, elderly persons, diabetics, and patients with a congenitally underdeveloped or defective immune system.

(B) Cytomegalovirus

Morphologically and structurally similar to other human herpes viruses, CMV causes a vision-threatening retinitis in AIDS patients. CMV retinitis has been treated with gancyclovir and/or foscarnet, but with only limited success.

The present inventor has observed that CMV-induced retinitis responds to HCG treatment. Thus, her invention further contemplates that HCG will synergize with other treatment modalities, such as gancyclovir or foscarnet, in the treatment of CMV-induced retinitis. According to this invention, HCG also will be used in the context of adjunctive therapy, in preparation for transplantation and other medical interventions which place a patient at risk for systemic life-threatening CMV infection. In addition, it is understood that HCG will be useful therapeutically after CMV infection has occurred. Support for using HCG in this regard is found in the observation that CMV infection is almost never active at the time of delivery of a human child, when HCG levels are high.

(C) Neonatal Applications

As noted above, HCG secreted by the placenta during pregnancy is believed to act as a natural immune-potentiator, in particular lending an antiviral activity which benefits the fetus. By the same token, it is a further aspect of the present invention that HCG will be administered to a baby at delivery and, optionally, for the first several months of life as well, until the infantile immune system matures, in order to prevent HIV transmission and control any low-level viremia. (Compare suggestion by Connor et al., *N. Eng. J. Med.* 331: 1173–89 (1994), to give the anti-HIV drug, zidovidine, during the last trimester of pregnancy and during delivery to impede HIV transmission from mother to child.) Moreover, the inventive HCG therapy, effected neonatally, should protect against various other viruses, including herpes viruses, such as CMV, and oncogenic viruses. Not all viral transmission is expected to be precluded, however, since rubella virus is communicated to the fetus from the pregnant woman, notwithstanding her high levels of HCG.

(D) Autoimmune Diseases

It now is recognized that many autoimmune diseases occur as a consequence of viral infections. Among such diseases are rheumatoid arthritis and ulcerative colitis, both of which are known to remit during pregnancy and flare at delivery. Other autoimmune diseases for which no viral etiology has been described, such as uveitis and psoriasis, likewise remit during pregnancy and flare at delivery. Accordingly, the present invention encompasses the use of exogenous HCG at high doses, to achieve blood levels at least comparable to HCG levels typically seen in a mother's blood during pregnancy, to control autoimmune diseases in adults.

(E) Prophylactic Applications

According to another aspect of the present invention, HCG will be administered prophylactically, in dosage regimens substantially similar to those described above, to persons—medical personnel, blood recipients, hemophiliacs, sexually active individuals, and HIV-negative recreational drug users, for instance—who are deemed at risk of exposure to HIV or who may have been exposed already to the virus. Prophylactic application of HCG also could benefit others who are at risk from disease, such as (i) travelers to areas affected epidemically by other, life-threatening viruses, such as HTLV-I and Ebola virus. More generally, HCG could be administered, in "rescue" fashion, immediately after a possible exposure to a variety of illnesses, the impact of which could be ameliorated by the immune-potentiating effect of the exogenous HCG.

(F) Vaccine Applications

In light of its immune-potentiating character, administration of HCG pursuant to the present invention will have the effect of a vaccine with respect to HIV, oncogenic viruses and the like, unless and until an effective vaccination approach is developed. A vaccine use of exogenous HCG also would be indicated in the event that an available vaccination for a specific condition is thought to involve even a moderate risk. Furthermore, when viral infections erupt for which there is no therapy or even a known etiology, as was the case in central Africa with the Ebola virus and in the southwestern United States with the hantavirus, uninfected individuals would have recourse to the inventive HCG therapy, in the reasonable hope that it will stop the particular virus involved, and infected patients also would be treated in an attempt to control the virus.

(G) Immune-System Remediation

The present invention comprehends treatment of individuals with HCG in instances where the immune system has been compromised or is to undergo compromise. Persons who could be treated in this context include, for example, cancer patients who are to start chemotherapy or irradiation which is expected to weaken or otherwise jeopardize their immune systems.

Contraindications for HCG are precocious puberty, prostatic carcinoma or other androgen-dependent neoplasms and a prior allergic reaction to HCG. Particular adverse reactions include headache, irritability, restlessness, depression, fatigue, edema, precocious puberty, gynecomastia, pain at the site of injection as well as various hypersensitivity reactions. Those administering HCG in accordance to the present invention should take into account these considerations.

In appropriate formulations that are known and conventional to those skilled in the art, the administration of HCG by various routes of administration is contemplated, including intramuscular, subcutaneous, transmucosal, transdermal and parenteral. As discussed above, administration of HCG is contemplated through a sustained-release drug delivery system, for example, transdermal skin patches and different types of implants. A bioavailable, sustained-release oral formulation of HCG also should be possible. Additionally, recombinant HCG should be feasible for human administration in this regard, allowing for an HCG-containing product that is purer, more concentrated and easier to administer.

It should be understood that this detailed description and the examples, while indicating preferred embodiments of the invention, are given by way of illustration. Various changes and modifications within the spirit and scope of the invention will be apparent to those skilled in the art from the description.

What is claimed is:

1. A method of treating or reducing the likelihood of a viral infection in a human patient suffering or at risk for suffering said infection, comprising (A) administering to said subject a clinically effective amount of human chorionic gonadotropin (HCG), wherein said effective amount is at least 10,000 IU, and then (B) monitoring said patient for parameters of said infection.

2. A method according to claim 1, wherein said virus is human immunodeficiency virus (HIV).

3. A method according to claim 1, wherein said virus is a Kaposi's Sarcoma-associated herpes virus.

4. A method according to claim 1, wherein said virus is of the genus Molluscipoxvirus.

5. A method according to claim 1, wherein said virus is a cytomegalovirus.

6. A method according to claim 1, wherein said effective amount is sufficient to produce an elevation in $T_8$ count or $T_4$ count of at least about 10% over pre-treatment levels in said patient after one month of therapy.

7. A method according to claim 1, wherein said patient is a neonate and step (A) is effected at delivery.

8. A method according to claim 1, wherein said effective amount is 150,000 IU per 70 kilograms of body weight.

9. A method according to claim 1, wherein said effective amount of said HCG is sufficient to produce a circulating concentration of HCG sufficient to suppress luteinizing hormone (LH) totally.

10. A method according to claim 9, wherein said effective amount is administered, three times a week, in a dosage ranging between about 10,000 and 20,000 IU.

11. Human chorionic gonadotropin hormone in a therapeutic, sustained-release form.

* * * * *